United States Patent [19]

Drauz et al.

[11] Patent Number: 5,026,925

[45] Date of Patent: Jun. 25, 1991

[54] METHOD OF PRODUCING CATECHOL AND HYDROQUINONE

[75] Inventors: Karl-Heinz Drauz, Freigericht; Axel Kleeman, Mülheim; Günter Prescher, Hanau; Gebhard Ritter, Darmstadt, all of Fed. Rep. of Germany

[73] Assignee: Degussa Aktiengesellschaft, Fed. Rep. of Germany

[21] Appl. No.: 7,351

[22] Filed: Jan. 27, 1987

[30] Foreign Application Priority Data

Jan. 25, 1986 [DE] Fed. Rep. of Germany ....... 3602180

[51] Int. Cl.$^5$ ...................... C07C 37/60; C07C 39/08
[52] U.S. Cl. ..................................... 568/771; 568/763
[58] Field of Search ................................ 568/771, 763

[56] References Cited

U.S. PATENT DOCUMENTS 4,533,766 8/1985 Drauz et al. ......................... 568/771
4,590,305 5/1986 Drauz et al. ......................... 568/771

FOREIGN PATENT DOCUMENTS 7312990 4/1974 Netherlands ........................ 568/771

Primary Examiner—Vivian Garner
Attorney, Agent, or Firm—Lawrence A. Hymo

[57] ABSTRACT

The nuclear hydroxylation of phenol can be carried out in an industrially very simple manner and with at least the yields obtained with the known methods as well as with very good selectivities by means of using aqueous hydrogen peroxide with the simultaneous addition of sulfur dioxide or selenium dioxide as catalyst.

6 Claims, No Drawings

METHOD OF PRODUCING CATECHOL AND HYDROQUINONE

BACKGROUND OF THE INVENTION

The invention is directed to the production of catechol and hydroquinone by hydroxylating phenol with aqueous hydrogen peroxide.

Catechol and hydroquinone are used in the manufacture of dyes, in the production of plastic as well as in the photo and plant-protective agent industry.

It is known according to German Patent 2064497 that the nuclear hydroxylation of aromatic compounds, especially of phenol, can be performed with hydrogen peroxide in the presence of a strong acid. The reaction medium should initially contain not more than 20 percent by weight water, preferably below 10 percent by weight.

The pH-$H_2O$ of the strong acids is stated to be under $-0.1$, preferably under $-1$. Sulfuric acid and perchloric acid appear to be preferred.

However, this method is evaluated rather negatively by the owner of German Patent 2064497 itself in its later patent German 2658545. Thus, the yields of hydroxylation products with the simultaneous usage of strong acids and of complexing agents for metals like pyrophosphoric acid are supposed to be "excellent". However, the degree of conversion of the aromatic compound was under 30%. In practice, there was not more than 4 to 10% degree of conversion.

This means a limitation of the productivity of the equipment and the recycling of a significant volume of initial material.

Therefore, as high a reaction speed as possible would be important. At a given temperature and amount of water this speed would be a function of the type and amount of the acid used. Independently of the type of acid, however, it would be desirable to increase the reaction speed without increasing the amount of acid, since the latter would be lost by being washed out and, moreover, the corrosion by the strong acid also cannot be ignored.

Thus, German Patent 2658545 suggests as an improvement to the method cited above the additional usage of aromatic aldehydes such as benzaldehyde together with the catalysts and stabilizers mentioned therein. Thus, the hydroxylation of phenol and substituted phenols with hydrogen peroxide takes place in the presence of strong acids, metal complexing agents and aromatic aldehydes.

Thus, instead of two components which influence the reaction, there are now used three. These components must not only be separated from the reaction mixture and are lost, since they are non-recoverable, but the "aromatic aldehyde" component is also subject to an oxidation with hydrogen peroxide, which includes the danger of contaminating the final product.

However, higher yields of approximately 70-76%, and in two instances of over 80%, also are obtained here only if phenol/hydrogen peroxide mole ratios of 20:1 and hydrogen peroxide of approximately 85% are used. However, as in German Patent 2064497, "a significant volume of initial material must be recycled" in these cases, which requires appropriate industrial systems. The reactors themselves must also be correspondingly large.

Since the yield of catechol and hydroquinone drops considerably when the mole ratio of phenol to hydrogen peroxide is reduced in the method of German Patent 2064497—at a ratio of 10:1 it is 60% and at a ratio of 5:1 it is 47%, see example 7—the presence of a large excess of phenol appears to be a necessity when carrying out the hydroxylation with strong acids, quite aside from the fact that the strong acids such as sulfuric acid and perchloric acid cited in German Patent 2064497 only had insufficient activity as catalysts.

Thus, the assumption had already been made that the catalytic action of the strong acids could be improved by using anhydrous solutions of hydrogen peroxide, of German Patent 2410742 and German Patent 2410758; however, here too, the presence of phosphorus compounds as complexing agents was also considered to be essential. It was pointed out in addition, that the reaction occurs most rapidly at high concentrations of acid. Thus, the question of corrosion by strong acids was not solved here either.

A considerable advance compared to the methods cited was achieved by the methods of DE-PS 3308737, DE-PS3308769, DE-PS3308763 and DE-PS 3308726, in which the hydroxylation of phenol or its derivates was performed by organic solutions of hydrogen peroxide in the presence of sulfur dioxide or selenium dioxide.

In these methods, the disturbing consequences of the strong acids such as corrosion did not occur, nor was it necessary, in order to raise the activity, to use additional compounds such as aldehydes or complexing agents such as phosphorus derivates.

Although the catalysts were used in very small amounts, the reaction speed was high; very advantageous space-time yields and very good yields were obtained. Due to the very slight amount employed, sulfur dioxide and selenium dioxide also require no special separation methods.

According to the state of the art, at first, only the use of anhydrous solutions of hydrogen peroxide appeared to result in better conversions and yields. However, when using strong acids as catalyst, there was still the problem of their separation as well as the occurrence of corrosion.

The use of sulfur dioxide or selenium dioxide achieved a considerable advance here. But even these methods required anhydrous solutions of hydrogen peroxide which were supposed to contain not more than 1% by weight, preferably under 0.5% by weight water. This procedure also requires additional systems for the separation and recycle of the organic solvent.

The present invention has the task of performing the hydroxylation of phenol with sulfur dioxide or selenium dioxide in an industrially simple form but with very good yields and selectivities.

SUMMARY OF THE INVENTION

It has now been found that this task can be solved if the hydroxylation of phenol is performed in the presence of sulfur dioxide or selenium dioxide using aqueous solutions of hydrogen peroxide. The mole ratio of phenol to hydrogen peroxide is 5 to 20:1, preferably 7 to 15:1, most preferably Hydrogen peroxide is used in commercially available solutions in the appropriate concentrations; 30-85% by weight solutions, preferably 70-85% by weight solutions are used.

The catalysts, sulfur dioxide or selenium dioxide, are used in an amount of 0.0001 to 0.01 mole per 1 mole of hydrogen peroxide.

Sulfur dioxide is used in liquid rr gaseous form from commercially available steel flasks or as solutions in inert solvents such as, e.g. phenol or alkyl esters, e.g. ethyl acetate. $SeO_2$ is used in the form of reagent purity.

The conversions are performed at temperatures of 40°–160° C. The pressure is not critical; in general, the process is performed at normal pressure.

The method can be performed either discontinuously or continuously. The phenol recycled in the method of the invention requires no special treatment. Preferably, the phenol consumed by the conversion is added before the excess phenol is distilled off.

The technical advance of the method of the invention resides first of all in its simple industrial execution. Instead of organic hydrogen peroxide solutions, aqueous hydrogen peroxide can be added directly. In addition, using sulfur dioxide or selenium dioxide in extremely small amounts avoids the problems which occur when strong acids are used, such as an expensive separation of these catalysts and the appearance of corrosion. Also there is eliminated the salting of the waste water by neutralization of the acids.

In addition, activators for a sufficient reaction speed are not necessary with sulfur dioxide and selenium dioxide, just as the addition of stabilizers is not necessary. This avoids additional industrial devices and also, given the sensitivity to oxygen of the effective activators in particular, a contamination of the final product by oxidation products of the activators. Moreover, the high reaction speed results in an increased space-time yield.

In addition to the simplified industrial execution, there is also the fact that the conversion of hydrogen peroxide is high and the yield of catechol and hydroquinone is at least as great as in the methods of the state of the art. Since the non-converted hydrogen peroxide decomposes and does not result in by-products, the selectivity is also great in the method of the invention.

These yields can also be obtained at a ratio of phenol to hydrogen peroxide which is reduced compared to the state of the art, see, examples 1–3 and 4. The dependency of the yields on the amount of the excess phenol is thus not as great as in the known methods which work with aqueous hydrogen peroxide.

The invention is explained in more detail in the following examples. The sulfur dioxide used is 99.75% by weight. The results were determined with high-pressure liquid chromatography (HPLC) and gas-liquid chromatography (GLC).

The work was performed under nitrogen, although no changes in the results were observed in the presence of air either.

The process can comprise, consist essentially of or consist of the stated steps with the recited materials.

"%"-specifications always are weight percents.

EXAMPLE 1

94g (1.0 mole) of distilled phenol are heated to 50° C. in a multi-neck flask under $N_2$ atmosphere. 0.5 g of a 2.5% by weight solution of sulfur dioxide in phenol and 2 g (0.05 mole) of 85% by weight hydrogen peroxide are gradually added to this agitated mixture. The temperature rises thereafter to 87° C.

After only 5 minutes there is determined a hydrogen peroxide conversion of 98% and after 10 minutes the $H_2O_2$ is completely converted.

The reaction mixture then contains 3.0 g of catechol and 1.65 hydroquinone, which corresponds to a total yield of dihydroxybenzenes of 84.5% based on the hydrogen peroxide used.

EXAMPLE 2

949 (1.0 mole) of distilled phenol are heated under an $N_2$ atmosphere to 110° C. 2.59 g (0.05 mole) of 70% hydrogen peroxide and 0.5 g of a 2.7% by weight solution of sulfur dioxide in phenol are gradually added to this agitated mixture. The temperature in the reaction solution rises thereafter, to 143° C.

After the exotherm died down, a hydrogen peroxide conversion of 99.6% was determined after 10 minutes.

The reaction mixture then contains 1.55 g hydroquinone and 3.1 g of catechol, which corresponds to a total yield of 82% based on the hydrogen peroxide used.

EXAMPLE 3

94 g (1.0 mole) of distilled phenol are heated under an $N_2$ atmosphere to 110° C. and gradually compounded with 3.5 g (0.05 mole) of 50% $H_2O_2$ and 0.5 g of a 3.0 % by weight solution of sulfur dioxide in phenol. The temperature in the reaction solution rose thereafter to 118° C.

After the exotherm died down, a hydrogen peroxide conversion of 80, 92 and 99.8% was determined after 10, 20 and 40 minutes.

The reaction mixture then contains 3.16 g of catechol and 1.45 g of hydroquinone, which corresponds to a total yield of dihydroxybenzenes of 83.5% based on the hydrogen peroxide used.

EXAMPLE 4

47g (0.5 mole) of distilled phenol are heated in a multi-neck flask under $N_2$ atmosphere to 110° C. 0.5 g of a 2.7% by weight solution of sulfur dioxide in phenol and 2.44 g (0.05 mole) of a 70% hydrogen peroxide are added to this solution. The temperature in the reaction solution rises thereafter to 146° C. After the exotherm died down, the following $H_2O_2$ conversions were determined after specific time intervals:

| $H_2O_2$ conversion | $H_2O_2$ yield |
|---|---|
| 2 minutes = 93.5% | 78.5% |
| 5 minutes = 96.8% | 79.8% |
| 10 minutes = 99.2% | 80.7% |

The reaction mixture then contains 1.25 g of hydroquinone and 3.19 g of catechol after 10 minutes, which corresponds to a total yield of 80.7% in relation to hydrogen peroxide used.

43g of phenol were found again which corresponds to a phenol selectivity of 94%.

EXAMPLE 5

47 g (0.5 mole) of distilled phenol are heated in a multi-neck flask under $N_2$ atmosphere to 110° C. 0.5 g of a 2.5% solution of sulfur dioxide in n-propyl acetate and 4.86 g (0.1 mole) of 70% hydrogen peroxide are added to this solution.

The temperature in the reaction solution rises thereafter to 133° C.

The following $H_2O_2$ conversions were measured after 2, 5 and 10 minutes:

| |
|---|
| 2 minutes = 83% |
| 5 minutes = 98% |

-continued

| | |
|---|---|
| 10 minutes = | 99.3% |

After 10 minutes, the reaction mixture contains 1.96 g of hydroquinone and 4.96 g of catechol, which corresponds to a total yield of 62.9% based on the hydrogen peroxide used.

EXAMPLE 6 (REFERENCE EXAMPLE)

47 g (0.5 mole) of distilled phenol are heated in a multi-neck flask under $N_2$ atmosphere to 110° C. 8 mg (0.25 mmole) of sulfur is added to this mixture and 2.43 g (0.05 mole) of 70% hydrogen peroxide are added after the sulfur has completely dissolved. The reaction temperature in the solution remained unchanged at 110° C. The following $H_2O_2$ conversions were determined in the following time intervals:

| $H_2O_2$ conversion | $H_2O_2$ yield |
|---|---|
| 2 minutes = 8% | 0% |
| 15 minutes = 20.4% | 10.8% |
| 30 minutes = 25% | 12.0% |

This reference example to Example 4 shows that $SO_2$ is the considerably better catalyst when an equimolar addition of catalyst is used. The indicated hydrogen peroxide yields refer to the hydrogen peroxide employed.

EXAMPLE 7 (REFERENCE EXAMPLE)

47 g (0.5 mole) of distilled phenol are heated in a multi-neck flask under $N_2$ atmosphere to 110° C. 25 mg (0.24 mmole) of 96–98% sulfuric acid and 2.43 g (0.05 mole) of 70% hydrogen peroxide solution are added to this solution.

The temperature in the solution rises thereafter to 136° C.

The following $H_2O_2$ conversions were determined after 2, 5 and 10 minutes:

| $H_2O_2$ conversion | yield dihydroxybenzenes |
|---|---|
| 2 minutes = 64% | 50.1% |
| 5 minutes = 94% | 72% |
| 10 minutes = 98.9% | 74% |

The indicated dihydroxybenzene yields are based on the hydrogen peroxide used. This reference example to Example 4 shows that $SO_2$ is a considerably better catalyst when an equimolar addition of catalyst is used.

EXAMPLE 8

(CONTINUOUS METHOD OF OPERATION)

135 g (85%) of hydrogen peroxide dissolved in 3540g phenol is added per hour into a vertical glass flow tube. The desired amount of gaseous $SO_2$ is dosed via a nozzle into this mixture. The $SO_2$ concentration of this mixture is 0.01 mole based on 1 mole of hydrogen peroxide used. This reaction mixture was heated before reaching the flow tube over a heat exchanger to the desired reaction temperature of 140° C. After 60 seconds dwell time, the $H_2O_2$ conversion was determined at the end of the the flow tube at 98.5% with a hydrogen peroxide yield of dihydroxybenzenes 86.3%. The quotient catechol to hydroquinone was determined to be 1.8. The mole ratio of phenol to hydrogen peroxide was 11.1 : 1.

It is claimed:

1. A method of producing catechol and hydroquinone comprising the nuclear hydroxylation of phenol with aqueous hydrogen peroxide in the presence of sulfur dioxide or selenium dioxide.

2. A method according to claim 1, wherein the mole ratio of phenol to hydrogen peroxide is between 7 to 15:1.

3. A method according to claim 1 wherein the mole ratio of phenol to hydrogen peroxide is 10:1.

4. A method according to claim 1 wherein 70–85% aqueous hydrogen peroxide solutions are used.

5. A method according to claim 2 wherein 70–85% aqueous hydrogen peroxide solutions are used.

6. A method according to claim 1 wherein 30–85% aqueous hydrogen peroxide solutions are used.

* * * * *

UNITED STATES PATENT AND TRADEMARK OFFICE
CERTIFICATE OF CORRECTION

PATENT NO. : 5,026,925

DATED : June 25, 1991

INVENTOR(S) : DRAUZ et al

It is certified that error appears in the above-identified patent and that said Letters Patent is hereby corrected as shown below:

ON THE TITLE PAGE, IN ITEM [75]

Please change: The second inventor's name "Axel Kleeman" to --Axel Kleemann--

Signed and Sealed this

Third Day of March, 1992

*Attest:*

HARRY F. MANBECK, JR.

*Attesting Officer*      *Commissioner of Patents and Trademarks*